United States Patent
Fukui et al.

[11] Patent Number: 5,855,201
[45] Date of Patent: Jan. 5, 1999

[54] GAS EXCHANGE APPARATUS

[75] Inventors: Yasuhiro Fukui, Tokyo; Akio Funakubo, Sagamihara; Koshiro Sato, Tokyo; Masanori Katayama, Hayama-machi, all of Japan

[73] Assignee: Fuji Systems Corporation, Tokyo, Japan

[21] Appl. No.: 720,052

[22] Filed: Sep. 27, 1996

[30]    Foreign Application Priority Data

Apr. 26, 1996 [JP] Japan .................................... 8-107524

[51] Int. Cl.$^6$ .......................... A61M 15/00; A61M 16/00; A61M 1/14; B01D 63/00
[52] U.S. Cl. ................................ 128/200.11; 128/200.24; 128/203.12; 128/203.25; 128/205.12; 422/44; 422/45; 210/321.6; 210/321.87
[58] Field of Search .......................... 128/200.11, 200.12, 128/200.13, 200.24, 203.12, 203.23, 203.25, 204.14, 205.12; 422/44, 45; 210/321.6, 321.87

[56]    References Cited

U.S. PATENT DOCUMENTS

| | | |
|---|---|---|
| 3,422,008 | 1/1969 | Mclain . |
| 3,969,240 | 7/1976 | Kolobow et al. ..................... 210/22 A |
| 3,994,988 | 11/1976 | Laurin ................................. 260/824 R |
| 4,336,138 | 6/1982 | Taniyama et al. .................... 210/321.4 |
| 4,444,662 | 4/1984 | Conover ............................... 210/500.2 |
| 4,876,066 | 10/1989 | Bringham et al. ........................ 422/46 |
| 4,975,247 | 12/1990 | Badolato et al. .......................... 422/48 |
| 5,137,531 | 8/1992 | Lee et al. .................................. 422/46 |
| 5,162,101 | 11/1992 | Cosentino et al. ........................ 422/46 |
| 5,188,801 | 2/1993 | Fini ........................................... 422/48 |
| 5,270,004 | 12/1993 | Cosentino et al. ........................ 422/46 |
| 5,376,334 | 12/1994 | Haworth et al. .......................... 422/46 |
| 5,472,613 | 12/1995 | Schofield ................................ 210/634 |
| 5,578,267 | 11/1996 | Cosentino et al. ........................ 422/46 |

*Primary Examiner*—David H. Willse
*Assistant Examiner*—Dinh X. Nguyen
*Attorney, Agent, or Firm*—Gifford, Krass, Groh, Sprinkle, Patmore, Anderson & Citkowski, P.C.

[57]    ABSTRACT

Disclosed is a small-sized gas exchange apparatus of high performance having an increased gas exchange rate and a reduced priming volume, comprising a hollow fiber module $M_1$ formed by bundling a plurality of silicone membrane hollow fibers 1 wound in the form of a twilled pattern, a housing $H_1$ for enclosing the hollow fiber module, an internal perfusion passage and an external perfusion passage formed within the housing $H_1$, a first inlet A and a first outlet B formed on the housing for gas or liquid for communication with the internal perfusion passage, and a second inlet C and a second outlet D formed on the housing for gas or liquid for communication with the external perfusion passage.

17 Claims, 5 Drawing Sheets

FIG.11

GAS EXCHANGE APPARATUS

BACKGROUND OF THE INVENTION

1. Field of the invention

The present invention relates to a gas exchange apparatus employing the silicone membrane hollow fiber for use as an artificial lung itself by being connected to the external blood circulation circuit, an artificial "ERA" as a liquid-to-gas phase gas exchanger, and further an oxygenator and disoxidizer for liquid and gas.

2. Brief Description of the Prior Art

As a conventional gas exchanger, there has been known a membrane-type artificial lung disclosed in Japanese Patent Publication No. 3-60508 (1991), in which gas exchange operation is performed through a porous gas exchange membrane having a plurality of minute or fine openings formed therethrough and serving as gas flow passages, wherein a kind of fine particles are maintained in the fine openings to reduce the sectional area, and, in addition, an anti-coagulant for blood is retained in the fine particles themselves or between these particles. Such a retention function of the agent contributes to prevent leakage of components of blood, such as water during a long term circulation. Such a retention function also prevents production of thrombus on the surface of gas exchange membrane, thereby the out-body circulation being enabled with a small amount of heparin supplement.

Another gas exchanger is disclosed using a "silicone membrane hollow fiber having a wall thickness of 50 to 150 micron", such as an anti-thrombus fiber type artificial lung disclosed in Japanese laid-open patent publication No. 63-97172, in which a hydrophilic monomer is graft-polymerized on the surface of a hollow fiber membrane, which is received in a housing, wherein blood is allowed to flow outside the hollow fiber membrane, and an oxygen-containing gas is allowed to flow inside the membrane. Using this artificial lung, since blood is allowed to come in contact with the outer surface of the membrane, the surface of which being anti-thrombus treated, the production of thrombus is advantageously hardly caused.

However, the gas exchange rate was not satisfactory in either of the conventional gas exchanger, since fine particles are confined in fine openings using "porous hollow fiber" for preventing sealum leakage in the first example, and "silicone membrane hollow fiber" having an increased wall thickness is used in the second embodiment. Therefore, there have been problems, when the exchange rate is increased, the dimension of the apparatus, that is, of the artificial lung increases, resulting in an increased quantity of blood, namely the priming volume, which is filled in the apparatus. In contrast, the reduced priming volume, although providing a small size, the quantity of gas exchange is accordingly decreased, and, therefore, the gas exchange rate is lowered.

SUMMARY OF THE INVENTION

Figure 1:
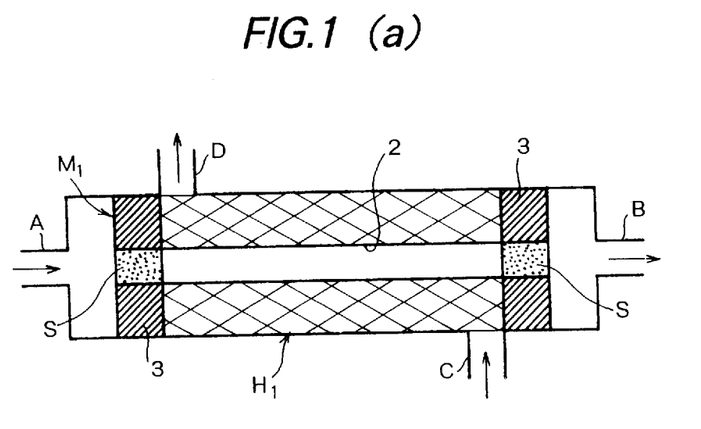
FIGS. 1a and 1b are sectional views schematically illustrating a gas exchange apparatus according to an embodiment of the invention.

As shown in FIG. 1, a gas exchange apparatus for use as an artificial lung according to the invention is fundamentally comprised of a hollow fiber module $M_1$ formed by bundling a plurality of silicone thin-walled hollow fibers wound in the form of a twilled pattern so as to form an internal perfusion passage and an external perfusion passage; a housing $H_1$ for enclosing said hollow fiber module; a first inlet A and a first outlet B formed on said housing $H_1$ for gas or liquid for communication with said internal perfusion passage; and a second inlet C and a second outlet D formed on said housing for gas or liquid for communication with said external perfusion passage.

DETAILED DESCRIPTION OF THE PREFERRED EMBODIMENTS

As the silicone membrane hollow fiber, the hollow fiber such as disclosed in prior patent application No.7-159899 (1995) filed by the same inventors may be used, which has not exceeding 400 microns in external diameter, not exceeding 50 microns in membrane thickness, and 100% elongation load strength of not lower than 5 g, composed of a silicone membrane composition including the following (a) to (e):

(a) 100 parts by weight of organo-polysiloxane having a viscosity of 10,000 to 10,000,000 poise;

(b) 5 to 50 parts by weight of organo-polysiloxane copolymer essentially formed of:

a triorganosiloxy monomer represented by the following formula: $R_3SiO_{1/2}$, where R is a non-substituted or substituted monovalent hydrocarbon group having 1 to 10 carbon atoms, and a $SiO_2$ unit; and having a molar ratio of said triorganosiloxy monomer relative to said $SiO_2$ unit being in the range of from 0.6 to 1.2;

(c) organohydrogen siloxane containing at least two hydrogen atoms each being of direct bonding with silicon atom;

(d) a catalytic quantity of platinum or a platinum compound; and (e) 100 to 150 parts by weight of finely powdered silica having a specific surface area of not less than 50 $m^2/g$.

The above hollow fiber 1 is prepared including a step of extruding the above silicone rubber component with heating and vulcanizing using a vulcanizing chamber to be elongated, wherein the ratio of the sectional area $S_1$ of the tube being extruded between a die and a nipple relative to the sectional area $S_2$ of the tube after being extruded, that is, the ratio $S_1$ by $S_2$ being a value between 1:0.5 to 1:0.01.

A hollow fiber module $M_1$ is fabricated in that, as shown in FIG. 1, the silicone membrane fiber 1 is wound around a core 2 in the form of twill figure with the angle of 30° to 160°, with the hollow fibers at both ends being sealed with silicone resin to each other, and thereafter the sealed portions 3 are cut out in the radial direction to allow the ends of the hollow fiber 1 to be freed. Therefore, the module $M_1$ is in the form that hollow fibers 1 each having a predetermined length are bundled in the twill form around the core 2 and the cross section thereof is circular.

The silicone rubber hollow fiber 1 may be, in the range of not exceeding 400 microns in diameter and not exceeding 50 microns in wall thickness, of the same internal and external diameters, or a plurality of kinds thereof having the same internal diameter but having each external diameter different from each other may be used.

The bundling density of the hollow fiber may be either uniform or ununiform. The volume ratio, that is, the volume occupied by the hollow fibers within the housing, may be preferably 10 to 70%.

As shown in FIG. 1, the housing $H_1$ is formed as a cylinder in section with the ends thereof being closed, wherein a first inlet A and a first outlet B are formed on both end walls of housing $H_1$, respectively. A second inlet C and outlet D are formed on the side wall of housing $H_1$ with a predetermined distance therebetween in the opposite radial direction to each other. Housing $H_1$ may have also an elliptic section, whereby the module $M_1$ may have an elliptic section, Hollow fiber module $M_1$ is received within the housing $H_1$, the ends being sealed with silicone resin, and the core 2 is closed at both ends also with silicone resin.

As mentioned above, in the enclosed state, the internal and external circulation passages for the module $M_1$ are formed within the housing $H_1$. The internal passage being formed inside the hollow fibers is in communication with the first inlet A and first outlet B, while the external passage being formed outside the silicone wall is in communication with the second inlet and outlet passages C and D.

Figure 2:
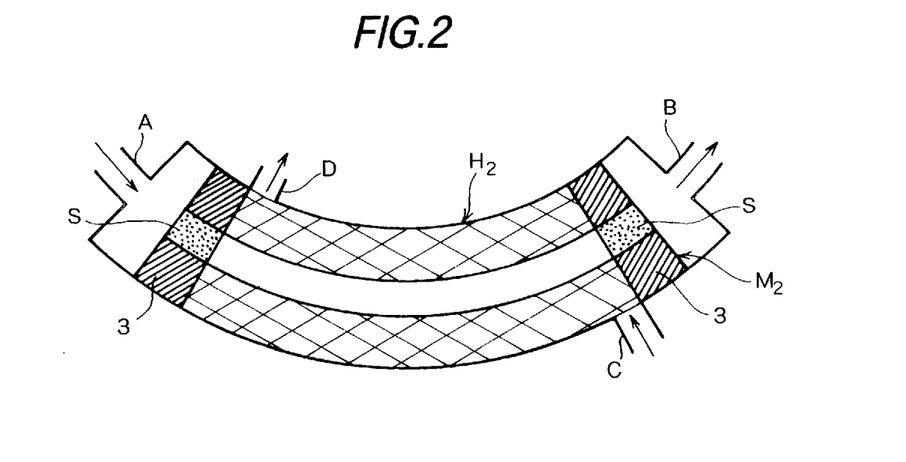
FIG. 2 is a sectional view schematically illustrating a gas exchange apparatus according to another embodiment.
Figure 3:
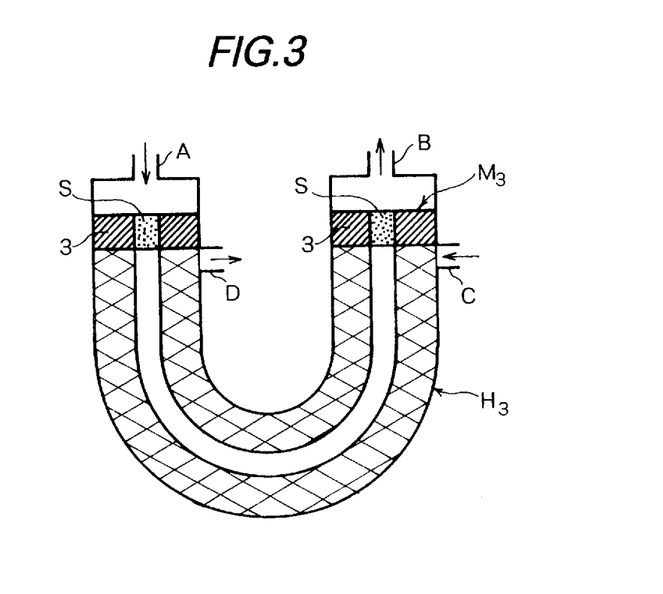
FIG. 3 is a sectional view schematically illustrating a gas exchange apparatus according to a further embodiment.

Gas exchangers shown in FIGS. 2 to 9 are those modified from that shown in FIG. 1. These are also included in the scope of the invention. Those shown in FIGS. 2 and 3 are different from that in FIG. 1 in the shape of the housings $H_2$ and $H_3$, respectively. Namely, these housings are modified in a curved form and a U-shaped form, respectively.

Figure 4:
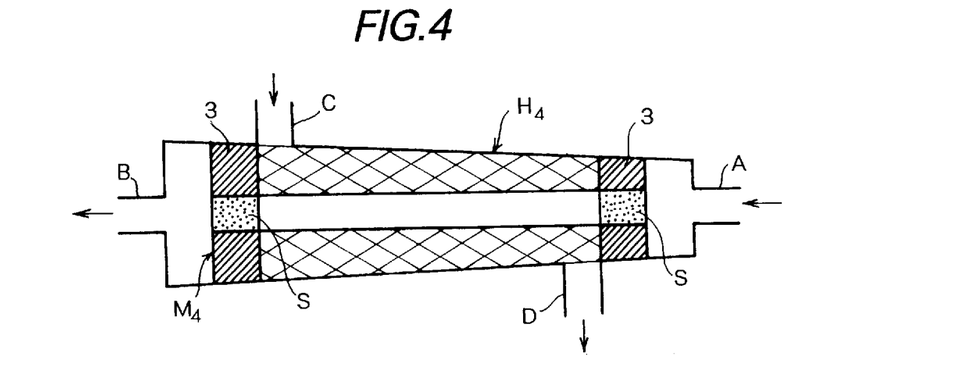
FIGS. 4, 5 and 6 are sectional views schematically illustrating each gas exchange apparatus according to embodiments similar to but modified from those in FIGS. 1, 2 and 3, respectively.
Figure 5:
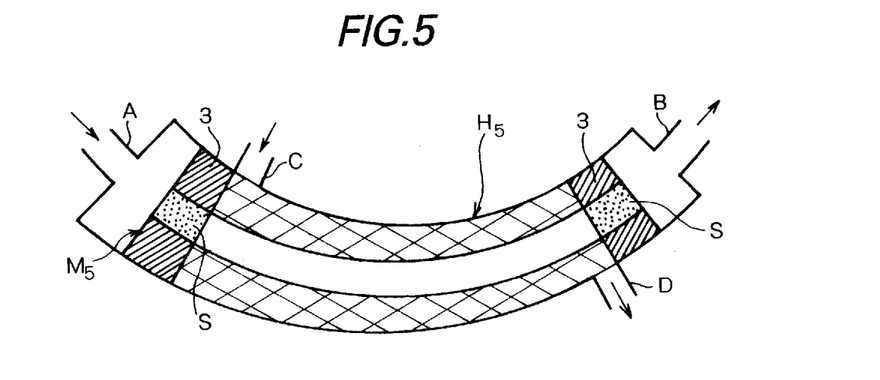
Figure 6:
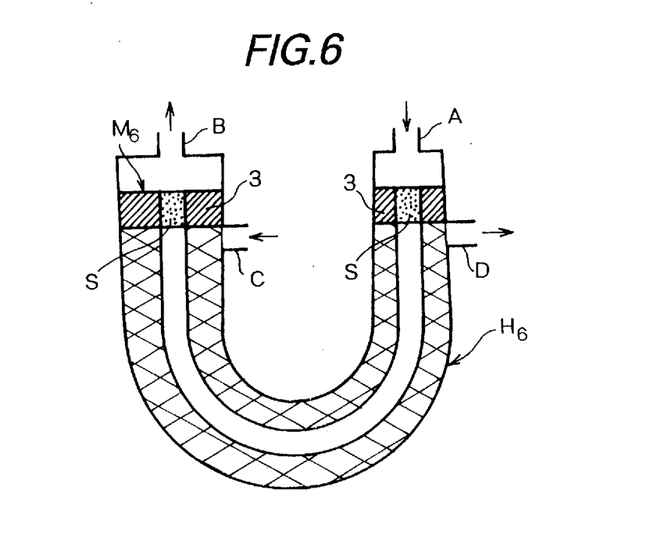

Similarly, housings $H_4$, $H_5$ and $H_6$ in FIGS. 4, 5 and 6 are modified form FIGS. 1, 2, and 3 so as to be gradually slimmed from one end to the other end along the axial direction of the housing.

The hollow fiber modules $M_2$, $M_3$, $M_4$, $M_5$ and $M_6$ are received into the housings H2, $H_3$, $H_4$, $H_5$ and $H_6$, respectively, after removing the cores from each housing. When preparing the modules $M_4$ to $M_6$ in twill wound form, the bundling density of the minor diameter is relatively larger than the major.

Figure 7:
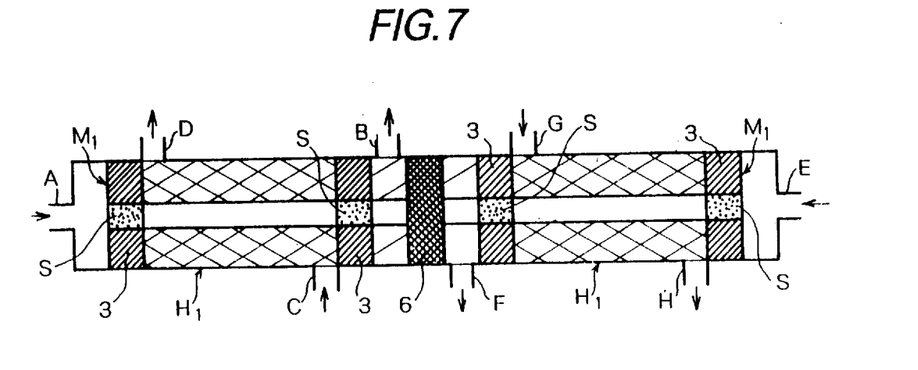
FIGS. 7, 8 and 9 are sectional views schematically illustrating each gas exchange apparatus according to each of further modified embodiments, respectively.

A gas exchanger shown in FIG. 7 is of the form of two exchangers in FIG. 1 combined in series together with a partition 6 interposed therebetween, having the first inlets A and E, first outlets B and F, second inlets C and G, and second outlets D and H.

The use of such a gas exchanger of the series type is as follows: with the first inlet E of the one device being closed, by lowering the pressure through the first outlet F, the venous blood is introduced from the inlet G and discharged from the outlet H; thus the gases $CO_2$, $N_2$ and $O_2$ are extracted from the venous blood. The blood is further introduced to the second inlet C, and added with $N_2$ and $O_2$ which are introduced through first inlet A and further added with a small amount of $CO_2$ to convert the blood to the arterial blood, which is collected from the second outlet D.

Figure 8:
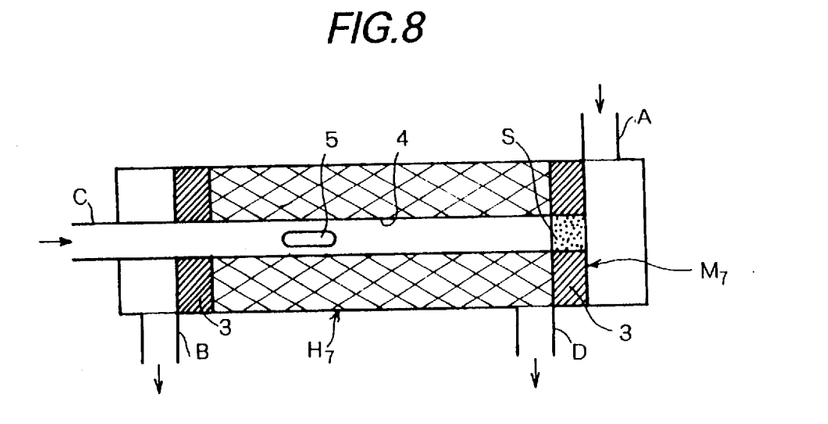

A gas exchanger shown in FIG. 8 is provided with a core 4 of the hollow fiber module $M_7$, the core 4 being extended out of the housing $H_7$ to form a second outlet C in communication with the external perfusion passage: from such second outlet C and through an opening 5 formed in the core 4, a liquid or gas is vented to an external perfusion passage and exhausted from the second outlet D.

Figure 9:
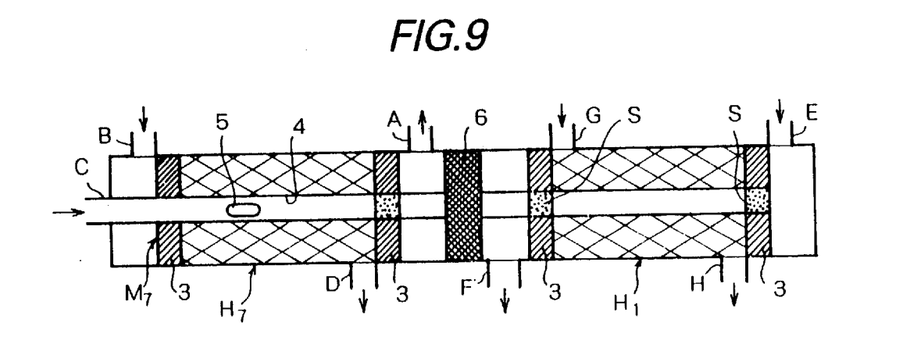

The gas exchanger in FIG. 9 is formed so that the left device of the apparatus shown in FIG. 7 is replaced by the gas exchanger of FIG. 8.

The fundamental structures in FIGS. 2 to 9 other than described above are not essentially different form that in FIG. 1.

According to the invention, any elongation or excessive wound stress or the like of the hollow fiber is prevented even if a considerable tension is applied, because of using a silicone membrane fiber having a thin wall thickness but having sufficient toughness.

Therefore, the hollow fiber may be formed if an arbitrary density, thereby enabling the volume ratio of the silicone membrane hollow fiber relative to the internal volume of the housing to be arbitrarily set. At this time, by using the different size of hollow fibers, the same effect can be achieved as changing the bundling density.

According to the invention, the filling density of silicone membrane hollow fibers in the hollow fiber module, the crossing angle of the hollow fibers, as well as the volume ratio between the occupied area of fibers and the internal volume of the housing (the hollow fiber filling density), may be also arbitrarily selected. Also, the configuration of the housing may be arbitrarily selected.

Accordingly, the flow of liquid within the internal and external perfusion passages, more particularly the disturbance flow of the gas or liquid are adequately controlled, thereby the gas exchange rate being increased to allow the apparatus to be small-sized and the priming volume to be reduced.

Hereinafter described are the preparation of the artificial lung and an in vitro evaluation thereof. The gas exchanger shown in FIG. 1 as an artificial lung has been prepared through the following procedures:

A. Preparation of an artificial lung:

Using the composition comprising the components (a) to (e), each of silicone membrane hollow fiber, having an external diameter of 400 microns, wall thickness of 50 microns, and tensile weight ($M_{100}$) of 5 gram, was prepared. A number of hollow fibers above were twill wound and bundled to form the modules $M_1$ of the types I and II, each of which was enclosed within each housing $H_1$ of types I and II to form an internal perfusion passage and an external perfusion passage in each housing $H_1$, for communicating with first inlet A and outlet B, and for communicating with second external inlet C and outlet D, respectively.

A hollow fiber module of type I:
  4000 pieces of silicone membrane hollow fibers 1 were uniformly twill bundled around a core having an external diameter of 8 mm, with a crossing angle of 120° to form a cylindrical module having an external diameter of 50 mm, a length of 200 mm and a length of each sealed end 3 being 5 mm.

A hollow fiber module of type II:
  A cylindrical module having an external diameter of 57 mm, a length of 200 mm and a length of each sealed end portion 3 being 8 mm: formed of 4600 pieces of silicone membrane hollow fibers uniformly twill bundled around a core having an external diameter of 8 mm, with a crossing angle of 120°.

A housing of type I:
  An end closed housing formed of polycarbonate in a cylinder having an internal diameter of 48 mm and a length of 200 mm, provided with a first inlet A, an first outlet B, a second inlet C and a second outlet D.

A housing of type II:

A cylindrically formed housing having both ends thereof closed, formed of polycarbonate, having an internal diameter of 55 mm, and a length of 200 mm, provided with a first inlet A, a first outlet B, a second inlet C, and a second outlet D.

Each of modules $M_1$ of types I and II above includes silicone membrane hollow fibers 1, wherein the fibers were sealed at both ends with silicone resin, thereafter the sealed portions were cut away along the radial direction.

The volume ratio of silicone membrane hollow fibers relative to the sectional area of the housing $H_1$ was 35%. The effective membrane area of the housing $H_1$ was 1.6 $m^2$ in the case using the type I, and 2 $m^2$ in the case of type II.

The breakdown strength of the membrane of silicone hollow fiber 1 was from about 950 to 2100 $g/mm^2$, which was twice that of the conventional silicone membrane hollow fiber.

The internal and external perfusion passages were formed by sealing the housing $H_1$ with the second portion 3 of module $M_1$ with silicone resin, and closing the both ends with also silicone resin.

In the closed state of module $M_1$ within housing $H_1$ in either case of type I or II, an internal and an external perfusion passage for fiber module $M_1$ are formed in the housing $H_1$. The first inlet A together with the first outlet B provides the entrance/exit for internal perfusion passage, while a second inlet C and a second outlet D provides the entrance/exit for external perfusion passage.

Figure 10:
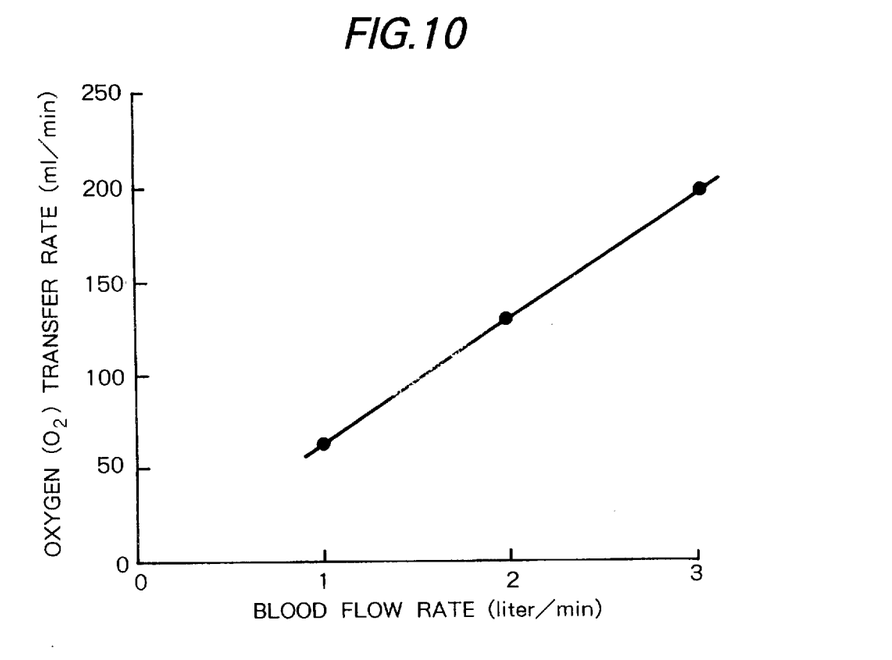
FIG. 10 is a diagram illustrating the gas exchange ability according to the invention.

In practice of the embodiment, three pieces of artificial lungs of type I each comprising a hollow fiber module of type I together with a housing of type I, and, three pieces of artificial lungs of type II each comprising a hollow fiber module of type II (see FIG. 10) together with a housing of type II, were prepared, each of which was evaluated in vitro as follows.

B. Evaluation of artificial lungs in vitro:

Evaluation in vitro was performed using fresh cow blood in such a manner that preparing 20 liters of the blood added with ACD-A solution as the anti-coagulant at the collecting time, which was converted to the standard venous blood by a commercially available artificial lung to be subjected to evaluation in vitro. The blood was fed to the external perfusion passage, and oxygen (by gas state) was supplied through the internal perfusion passage.

The blood circuit was formed by a tube having an inner diameter of ⅜ inch connected to second inlet C and outlet D and a boat for collecting blood and measuring the pressure was provided adjacent the inlet C and outlet D. The blood circulation was carried out by a roller pump attached to the tube.

The rate of blood flow was 1, 2 or 3 liter/min, oxygen flow in the artificial lung of type I was by the ratio of oxygen flow Q versus blood flow V (V/Q) being 1 and 2, while the ratio was 1 in the case of the lung of type II.

For reference of mechanical strength, water was filled to the blood side and gas side, with applying an additional pressure of 500 mmHg to the blood side, the volume variation at the gas side was obtained based on the overflown value of filled water. At the same time, a pressure was applied on the gas side in order to obtain the volume change of the blood side.

Figure 11:
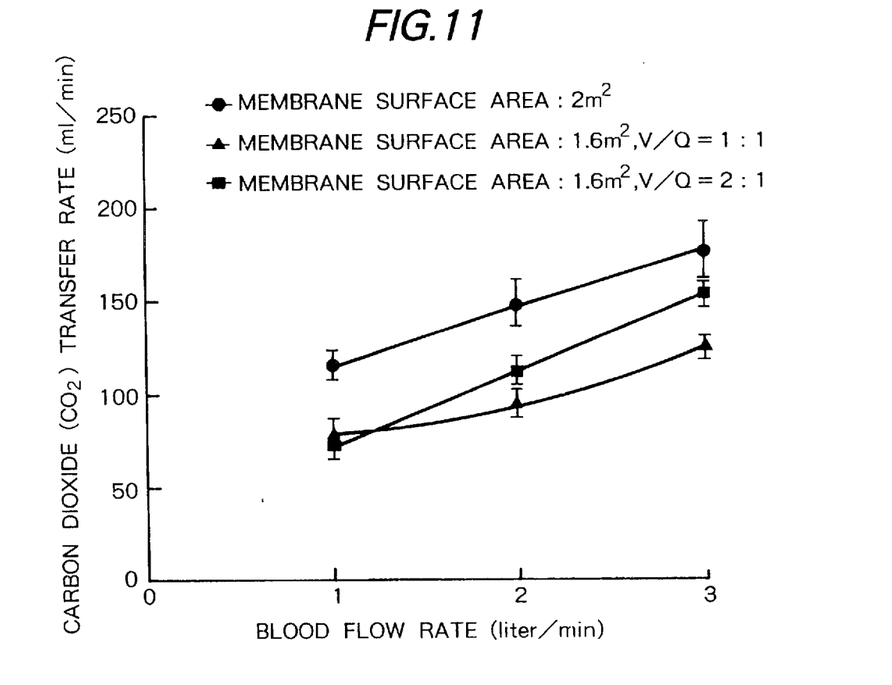
FIG. 11 is another diagram illustrating the gas exchange ability according to the invention.

C. Result of Evaluation:

As to oxygen ($O_2$) transfer rate, in either artificial lung of types I and II, the oxygen saturation rate by each flow rate of blood at the side of second outlet D was as high as 99 to 100%. The transfer rate of carbon dioxide using the lung of type I at a flow rate of 3 liter/min was 108 to 112 ml/min (milliliters per minute) at V/Q=1, and 140 to 146 ml/min at V/Q=2 (see FIG. 11). Accordingly, by increasing the gas flow rate, the transfer rate was increased by 30%.

On the other hand, the transfer rate of carbon dioxide was in the range of from 158 to 164 ml/min in the case using the lung of type II at the same blood flow rate.

The pressure loss was increased in proportion with the blood flow rate in either of the lungs of types I and II, the value of which being 196.64 mmHg at a blood flow rate of 3 liter/min.

The blood filling volume (priming volume) was 150 ml(milli liter) by the lung of type I, and 240 ml by the lung of type II. The change of the blood filling volume caused by additional pressure was measured: as a result, the volume change rate was, at either of the gas side and blood side, in the order of 0.2 to 0.3 ml, which corresponds to 0.1% or so of the blood filling rate.

In the anti-pressure test preliminarily performed, any explosion of the wall was not observed in the pressure range up to 5 $kg/cm^2$, corresponding to about 3,760 mmHg, which was applied on the gas side of the artificial lung.

In the evaluation on lungs of types I and II as to gas exchange ability, excellent performance was exhibited so that no difference was observed compared with the commercially available artificial lungs of porous polypropyrene membrane hollow fiber. Also, compared with the conventional lungs formed of silicone hollow fibers having a membrane area of 5 to 7 $m^2$, the gas exchange ability of the increased order was confirmed even with the wall area of about ⅓ compared with the conventional.

D. Conclusion:

From the result of in-vitro evaluation above, the following conclusion was obtained:

(1) It has been confirmed that the artificial lung using silicone walled hollow fibers has the gas exchange ability in the same order of that using polyethylene porous hollow fibers, and has a sufficient performance as an artificial lung.

(2) The silicone walled hollow fiber 1 of the invention has the dimension of about ½ that of the conventional silicone membrane hollow fiber. Therefore, according to the invention, compared with the conventional lung using the conventional silicone membrane hollow fibers, it has been possible to obtain a membrane area of nearly twice that of the conventional lung within the housing having the same volume.

Accordingly, it has been enabled to increase the gas exchange rate per unit volume and also to minimize the priming volume by either of artificial lungs of type I and type II, and thereby the apparatus has been small-sized.

As discussed above, the invention provides a small-sized gas exchange apparatus of high performance having an increased gas exchange rate and a minimized priming volume.

What is claimed is:

1. A gas exchange apparatus for use as an artificial lung comprising:

a flexible and freely bendable hollow fiber module formed as a cylindrical structure by bundling a plurality of silicone membrane hollow fibers wound in the form of a twilled pattern;

a housing for enclosing said hollow fiber module, said housing having an internal volume;

a circular cross section hollow core having two ends, said core having seals on the two ends, said seals being formed of a resin;

said cylindrical structure of said flexible and freely bendable hollow fiber module formed by bundling said plurality of silicone membrane hollow fibers wound on said core, in the form of aid twilled pattern, said silicone membrane hollow fibers each having two ends, an interior and an exterior diameter, the ends of said fibers being cut open and sealed to each other by said resin, so as to form an internal perfusion passage through the interior of said silicone membrane hollow fibers and an external perfusion passage between the exterior of said silicone membrane hollow fibers and the interior volume of said housing;

a first inlet and a first outlet formed on said housing for gas or liquid communication with said internal perfusion passage;

and a second inlet and a second outlet formed on said housing for gas or liquid communication with said external perfusion passage.

2. A gas exchange apparatus according to claim 1, wherein said hollow fiber having not exceeding 400 microns in external diameter, not exceeding 50 microns in membrane thickness, and 100% elongation load strength of not lower than 5 g, composed of a silicone membrane composition including:

(a) 100 parts by weight of organo-polysiloxane having a viscosity of 10,000 to 10,000,000 poise;

(b) 5 to 50 parts by weight of organo-polysiloxane copolymer essentially formed of:
a triorganosiloxy monomer represented by the following formula: $R_3SiO_{1/2}$, where R is a non-substituted or substituted monovalent hydrocarbon group having 1 to 10 carbon atoms, and
a $SiO_2$ unit; and having a molar ratio of said triorganosiloxy monomer relative to said $SiO_2$ unit being in the range of from 0.6 to 1.2;

(c) organohydrogen siloxane containing at least two hydrogen atoms each being directly coupled with silicon atom, the amount of the siloxane corresponding to an amount of supplying hydrogen atoms directly coupled with silicon atom being 0.5 to 10 times by mole relative to vinyl groups contained in said components (a) and (b);

(d) a catalytic quantity of platinum or a platinum compound; and (e) 100 to 150 parts by weight of finely powdered silica having a specific surface area of not less than 50 $m^2/g$.

3. The gas exchange apparatus according to claim 1 wherein the external diameter of each of said plurality is uniform, as compared to other fibers comprising said plurality.

4. The gas exchange apparatus according to claim 1 wherein the external diameter of each of said hollow fibers is nonuniform, as compared to the other fibers comprising said plurality.

5. The gas exchange apparatus according to claim 1 wherein said plurality of fibers are bundled, so as to have a uniform bundling density within said module.

6. The gas exchange apparatus according to claim 1 wherein said plurality of fibers are bundled, so as to have a nonuniform bundling density within said module.

7. The gas exchange apparatus according to claim 1, wherein the internal volume of said housing relative to the combined volume of said plurality of silicone membrane hollow fibers is in a volume ratio in the range of 10 to 70%.

8. The gas exchange apparatus according to claim 1 wherein said plurality of fibers are bundled in a twill figure having a crossing angle, so as to form said hollow fiber module, the crossing angle being in the range of from 30 to 160 degrees.

9. The gas exchange apparatus according to claim 1 wherein said housing is a cylindrical body having both ends closed, and having a shape selected from the group consisting of: straight, curved and bent forms.

10. A gas exchange apparatus for use as an artificial lung comprising:

a hollow fiber module formed by bundling a plurality of silicone membrane hollow fibers wound in the form of a twilled pattern wherein each of said plurality of hollow fibers is less than 400 microns in external diameter, less than 50 microns in membrane thickness, has an internal volume and 100% elongation load strength of more than 5 g, composed of a silicone membrane composition including:

(a) 100 parts by weight of organo-polysiloxane having a viscosity of 10,000 to 10,000,000 poise;

(b) 5 to 50 parts by weight of organo-polysiloxane copolymer essentially formed of:
a triorganosiloxy monomer represented by the following formula: $R_3SiO_{1/2}$, where R is a monovalent hydrocarbon group selected from a group consisting of: a non-substituted and a substituted form, the hydrocarbon group having 1 to 10 carbon atoms, and a $SiO_2$ unit;
and having a molar ratio of said triorganosiloxy monomer relative to said $SiO_2$ unit being in the range of from 0.6 to 1.2;

(c) organohydrogen siloxane containing at least two hydrogen atoms each being of direct bonding with silicon atom;

(d) a catalytic quantity of platinum or a platinum compound; and (e) 100 to 150 parts by weight of finely powdered silica having a specific surface area of more than 50 $m^2/g$;

a housing for enclosing said hollow fiber module having an internal volume;

an internal perfusion passage and an external perfusion passage formed within said housing;

a first inlet and a first outlet formed on said housing for gas or liquid for communication with said internal perfusion passage; and a second inlet and a second outlet formed on said housing for gas or liquid for communication with said external perfusion passage.

11. The gas exchange apparatus according to claim 10 wherein the external diameter of each of said plurality is uniform, as compared to other fibers comprising said plurality.

12. The gas exchange apparatus according to claim 10 wherein the external diameter of each of said hollow fibers is nonuniform, as compared to the other fibers comprising said plurality.

13. The gas exchange apparatus according to claim 10 wherein said plurality of fibers are bundled, so as to have a uniform bundling density within said module.

14. The gas exchange apparatus according to claim 10 wherein said plurality of fibers are bundled, so as to have a nonuniform bundling density within said module.

15. The gas exchange apparatus according to claim 10, wherein the internal volume of said housing relative to the combined volume of said plurality of silicone membrane hollow fibers is in a volume ratio in the range of 10 to 70%.

16. The gas exchange apparatus according to claim 10 wherein said plurality of fibers are bundled in a twill figure having a crossing angle, so as to form said hollow fiber module, the crossing angle being in the range of from 30 to 160 degrees.

17. The gas exchange apparatus according to claim 10 wherein said housing is a cylindrical body having both ends closed, and having a shape selected from the group consisting of: straight, curved and bent forms.

* * * * *

UNITED STATES PATENT AND TRADEMARK OFFICE
CERTIFICATE OF CORRECTION

PATENT NO. : 5,855,201
DATED : January 5, 1999
INVENTOR(S) : Yasuhiro Fukui et al.

It is certified that error appears in the above-identified patent and that said Letters Patent is hereby corrected as shown below:

Column 2, line 67, "3" should be --S--.
Column 3, line 67, "outlet" should be --inlet--.
Column 4, line 2, "outlet" should be --inlet--.
Column 5, line 23, after "$M_1$" insert --of types I and II--.
Column 5, line 57, after "type II" insert --see Fig. 10--.
Column 7, line 4, (claim 1), "aid" should be --said--.

Signed and Sealed this

Twenty-ninth Day of August, 2000

Attest:

Q. TODD DICKINSON

Attesting Officer

Director of Patents and Trademarks